(12) United States Patent
Alley

(10) Patent No.: US 10,932,697 B2
(45) Date of Patent: Mar. 2, 2021

(54) SYSTEM FOR ANALYZING A GOLF SWING AND/OR GOLF BALL FLIGHT PATH

(71) Applicant: Golf Cloud, Inc., St. Charles, IL (US)

(72) Inventor: John Alley, St. Charles, IL (US)

(73) Assignee: Golf Cloud, Inc., St. Charles, IL (US)

( * ) Notice: Subject to any disclaimer, the term of this patent is extended or adjusted under 35 U.S.C. 154(b) by 74 days.

(21) Appl. No.: 16/042,604

(22) Filed: Jul. 23, 2018

(65) Prior Publication Data

US 2020/0022625 A1 Jan. 23, 2020

(51) Int. Cl.
*A61B 5/11* (2006.01)
*A61B 5/00* (2006.01)
*A63B 24/00* (2006.01)
*G06K 9/00* (2006.01)
*A63B 69/36* (2006.01)
*A63B 102/32* (2015.01)

(52) U.S. Cl.
CPC .......... *A61B 5/1128* (2013.01); *A61B 5/0013* (2013.01); *A61B 5/0022* (2013.01); *A61B 5/0077* (2013.01); *A61B 5/6895* (2013.01); *A61B 5/7405* (2013.01); *A63B 24/0003* (2013.01); *A63B 69/36* (2013.01); *G06K 9/00986* (2013.01); *A61B 2503/10* (2013.01); *A61B 2560/0475* (2013.01); *A61B 2562/0204* (2013.01); *A61B 2576/00* (2013.01); *A63B 2102/32* (2015.10); *A63B 2220/806* (2013.01); *A63B 2220/808* (2013.01); *A63B 2225/20* (2013.01); *A63B 2225/50* (2013.01)

(58) Field of Classification Search
None
See application file for complete search history.

(56) References Cited

U.S. PATENT DOCUMENTS 9,238,165 B2 * 1/2016 Marty .................. A63B 63/083
2017/0361193 A1 * 12/2017 Molinari ............ A63B 24/0003

FOREIGN PATENT DOCUMENTS

| KR | 10-2012-0031680 | 4/2012 | |
|---|---|---|---|
| KR | 10-2016-0026493 | 3/2016 | |
| WO | WO-2017026664 A1 * | 2/2017 | ............... G06T 7/00 |

(Continued)

OTHER PUBLICATIONS

*IPong Expert—Great for Learning Table Tennis*, IPong, downloaded Jul. 23, 2019, http://www.ipang.net/joomla.

(Continued)

*Primary Examiner* — James M Anderson, II
(74) *Attorney, Agent, or Firm* — Dunlap Codding, P.C.

(57) ABSTRACT

A system for analyzing a golf swing is disclosed having an image processor, memory, a main processor, and a camera connected via a communications circuit. A cache of batteries provides power to the image processor, the memory, the main processor, the camera lens, and the communications circuit. An hourglass shaped, two component housing, is provided having a top housing supporting the camera and a bottom housing sized to receive and encapsulate the cache of batteries, said top housing component being operably attached to the bottom housing component such that the top housing component can rotate about a central axis of the bottom housing component and tilt from the central axis.

12 Claims, 4 Drawing Sheets

(56) References Cited

FOREIGN PATENT DOCUMENTS

WO     WO 2017-026664     12/2017

OTHER PUBLICATIONS

*App Store Preview—Shot Tracer*, Apple Inc., downloaded Jul. 23, 2019, https://apps.apple.com/us/app/shot-tracer/id1140451547.
*App Store Preview—Protracer*, Apple Inc., downloaded Jul. 23, 2019, https://apps.apple.com/us/app/protracer/id814443850.
*App Store Preview—Golf Shot Tracer*, Apple Inc., downloaded Jul. 23, 2019, https://apps.apple.com/us/app/golf-shot-tracer/id1317550678.
International Search Report and Written Opinion for Application PCT/US19/43055 dated Oct. 31, 2019.

\* cited by examiner

SYSTEM FOR ANALYZING A GOLF SWING AND/OR GOLF BALL FLIGHT PATH

BACKGROUND

A golf swing that results in a desirable golf ball flight path requires the synchronized actions of more than 80 different muscles in a way that is not particularly intuitive for most people. The requirement for complex and unnatural muscle movements is the principal reason why golf is considered to be a difficult game to master. Even if one is successful in correctly emulating the precise body movements of a given professional, it is unclear that the club movements that are actually produced are correct for a particular person given his or her physical build.

Prior inventions have used video recordings of the golf swings of various professional golfers for comparison to a student as though they were magic formulas. In fact, many professionals owe their success more to extensive practice than to excellent techniques. Since golf tournaments can be seen on national television every weekend, most of the techniques that amateur golfers would like to learn have become common knowledge and are practiced by most professionals. In the past, obtaining video recordings of an amateur's golf swing and/or golf ball flight path during actual play for analysis has been difficult. In prior art systems, bulky cameras or difficult to set-up systems have been used that do not lend themselves to use in everyday play or for the recording and analysis of each swing and/or ball flight path during a round. A need exists therefore, for a system that is compact, portable, and easy to use such that a golfer is inclined to record each swing and/or ball flight path during each round for analysis.

BRIEF DESCRIPTION OF THE SEVERAL VIEWS OF THE DRAWINGS

To assist those of ordinary skill in the relevant art in making and using the subject matter hereof, reference is made to the appended drawings, which are not intended to be drawn to scale, and in which like reference numerals are intended to refer to similar elements for consistency. For purposes of clarity, not every component may be labeled in every drawing.

DETAILED DESCRIPTION

Figure 1:
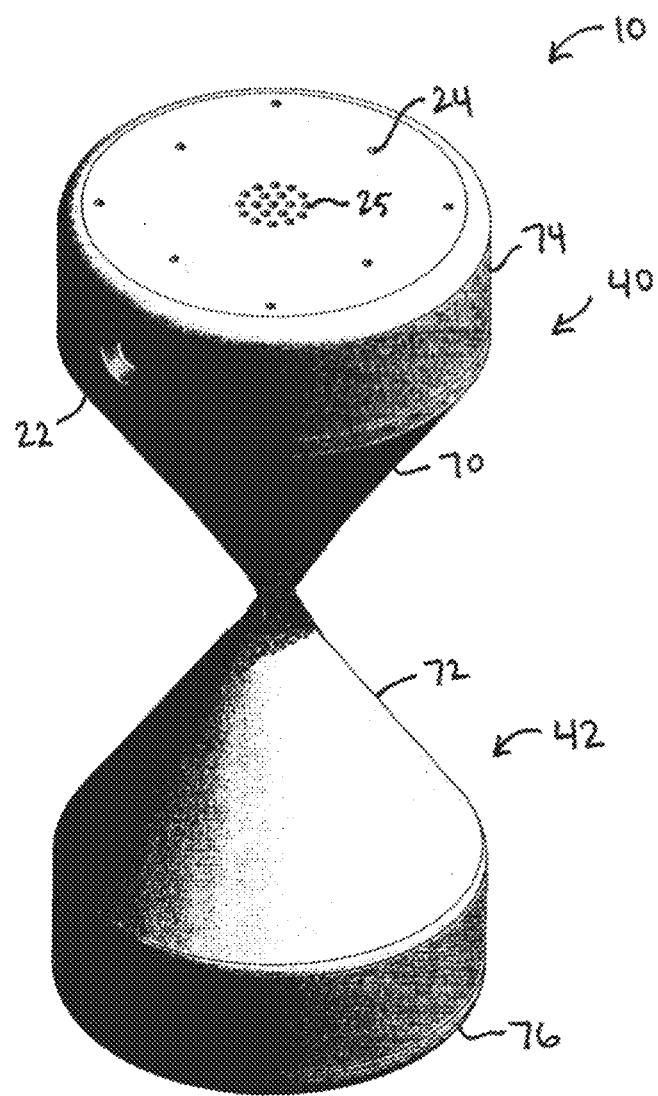
FIG. 1 is a front perspective view of a system for analyzing a golf swing and/or golf ball flight path constructed in accordance with one embodiment of the present disclosure.
Figure 1:
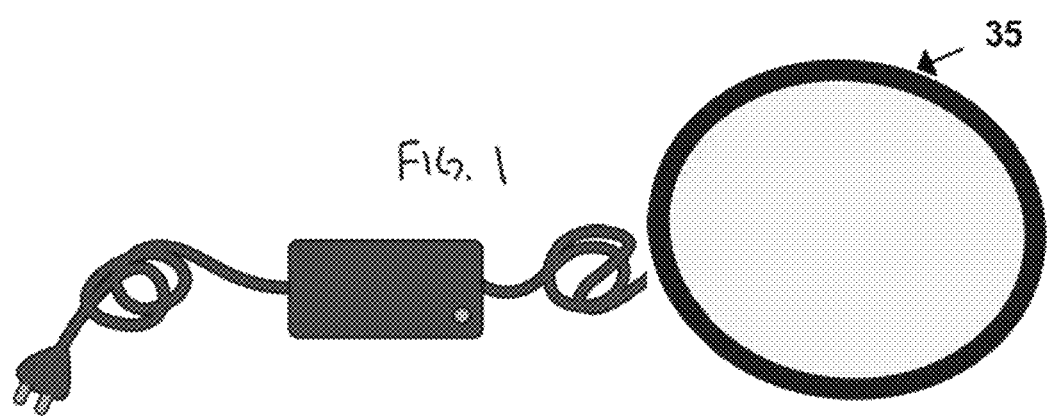

The present invention now will be described more fully hereinafter with reference to the accompanying drawings, which form a part hereof, and which show, by way of illustration, specific exemplary embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as a system or device. The following detailed description is, therefore, not to be taken in a limiting sense.

Before explaining at least one embodiment of the disclosure in detail, it is to be understood that the disclosure is not limited in its application to the details of construction, experiments, exemplary data, and/or the arrangement of the components set forth in the following description or illustrated in the drawings unless otherwise noted.

The systems described in the present disclosure are capable of other embodiments or of being practiced or carried out in various ways. Also, it is to be understood that the phraseology and terminology employed herein is for purposes of description, and should not be regarded as limiting.

The following detailed description refers to the accompanying drawings. The same reference numbers in different drawings may identify the same or similar elements.

As used in the description herein, the terms "comprises," "comprising," "includes," "including," "has," "having," or any other variations thereof, are intended to cover a non-exclusive inclusion. For example, unless otherwise noted, a process, method, article, or apparatus that comprises a list of elements is not necessarily limited to only those elements, but may also include other elements not expressly listed or inherent to such process, method, article, or apparatus.

Further, unless expressly stated to the contrary, "or" refers to an inclusive and not to an exclusive "or". For example, a condition A or B is satisfied by one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more, and the singular also includes the plural unless it is obvious that it is meant otherwise. Further, use of the term "plurality" is meant to convey "more than one" unless expressly stated to the contrary.

As used herein, any reference to "one embodiment," "an embodiment," "some embodiments," "one example," "for example," or "an example" means that a particular element, feature, structure or characteristic described in connection with the embodiment is included in at least one embodiment. The appearance of the phrase "in some embodiments" or "one example" in various places in the specification is not necessarily all referring to the same embodiment, for example.

Figure 2:
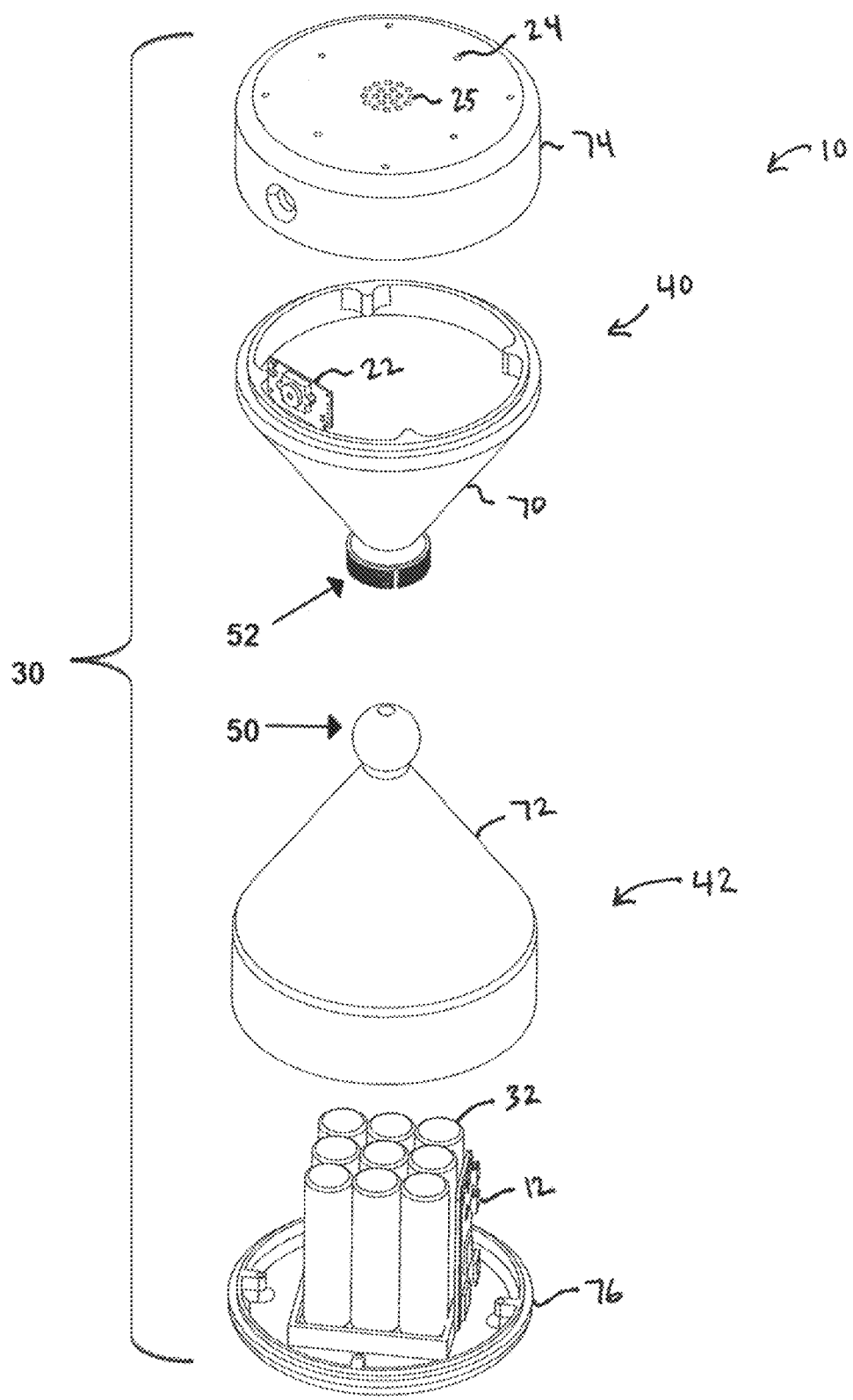
FIG. 2 is an exploded view of the system for analyzing a golf swing and/or golf ball flight path of FIG. 1.
Figure 3:
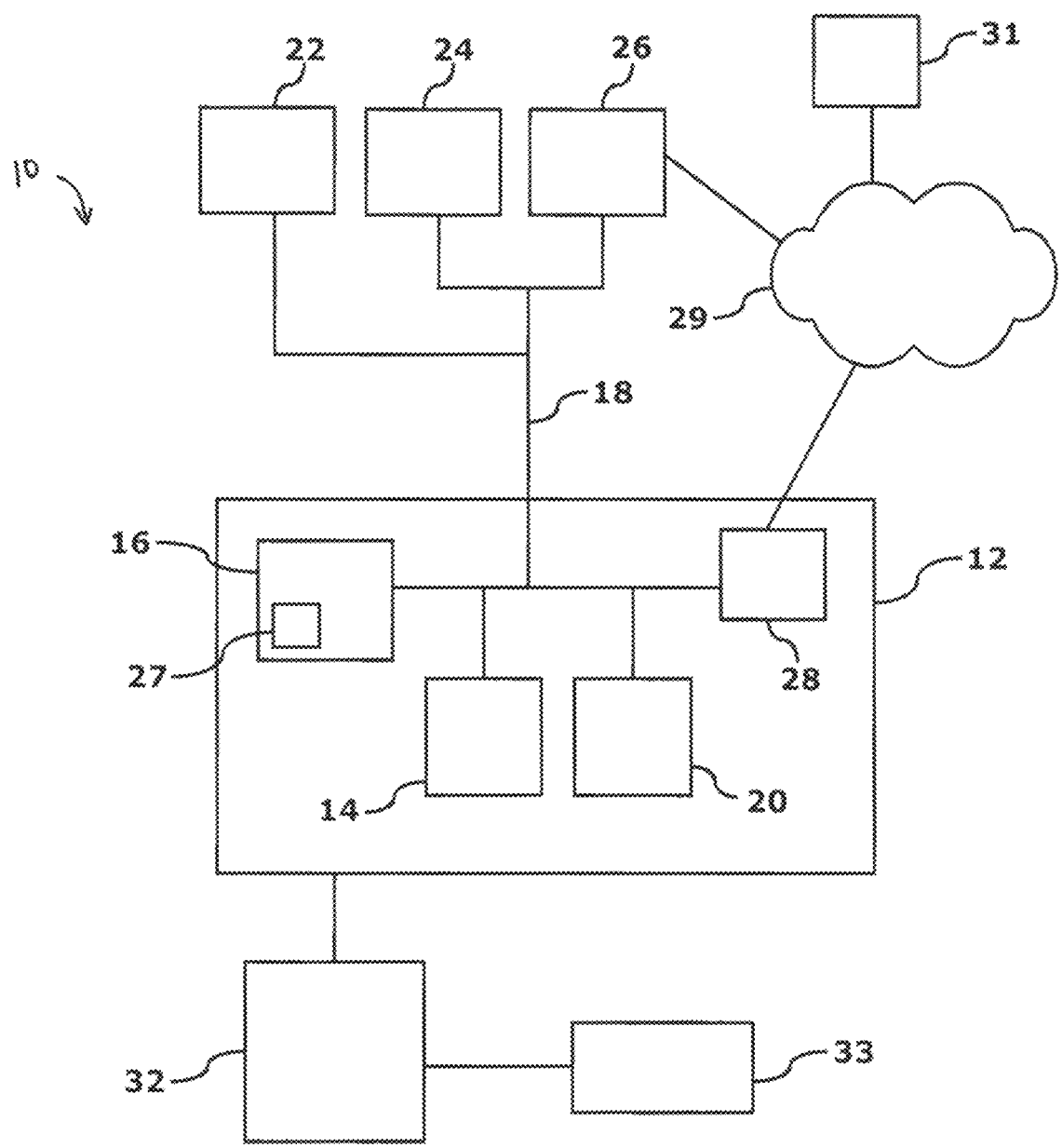
FIG. 3 is a block diagram of hardware forming an exemplary embodiment of the system for analyzing a golf swing and/or golf ball flight path of FIGS. 1 and 2.

Referring now to FIGS. 1-3, a system 10 for analyzing a golf swing and/or golf ball flight path constructed in accordance with the present disclosure is shown. In the embodiment illustrated in FIGS. 1-3, the system 10 is provided with an image processor 14, computer readable memory 16, a communications circuit 18, a main processor 20, a camera 22, a microphone 24, a speaker 25, a communications port 26, a wireless antenna 28, a two-component housing 30, and a cache of batteries 32. As illustrated in FIG. 3, at least the image processor 14, computer readable memory 16, and main processor 20 may be functionally disposed on a single microprocessor chip 12, which is sometimes referred to in the industry as a System On a Chip (SOC). As would be understood by those of ordinary skill in the art, the image processor 14 and main processor 20 may comprise the same circuitry under the control of firmware and/or software to achieve the imaging or main functions within the system 10.

The image processor 14, main processor 20, memory 16, camera 22, microphone 24, speaker 25, communications port 26, and antenna 28 may be operably connected via the communications circuit 18. The communications circuit 18 may be wireless, wired, or a combination of wired and wireless. The communications circuit 18 transmits and receives data in accord with one or more communications protocols selected from the group comprising 4G, 5G, Bluetooth, FTP, HTTP, HTTPS, MMS, PPP, SMTP, SMS, SSL, TLS, TCP/IP, and Wi-Fi, Wi-Max. The camera 22 is comprised of a lens and an image sensor. The image sensor converts the light entering the camera via the lens that forms an optical image into an electrical signal. The electrical signal generated by the image sensor is fed to the image processor via the communications circuit 18. The image sensor may be comprised of semiconductor charge-coupled devices (CCD), active pixel sensors in complementary metal-oxide-semiconductor (CMOS) or N-type metal-oxide-semiconductor (NMOS, Live MOS) technologies, or a combination of both MOS and CCD technologies. All image sensor technologies convert the photons (i.e. pieces of light that together comprise an image) that fall on the face of each imaging element into electrical signals that represent the portion of the image. Each technology has a slightly different performance characteristics that may make one technology more desirable than another depending on a variety of design choices. Regardless of the imaging technology used, a higher resolution sensor (i.e. more densely packed imaging elements) will be preferred in most instances in order to provide for the capture of better quality images.

The communications port 26 (shown in FIGS. 3 and 4) may be operably connected to the communications circuit 18 such that data can be transmitted and received over a wired connection. The communications port 26 may be any known connection for connecting to a network 29 via a wire. For instance, the communications port may be a universal serial bus (USB) connection, a modular connection such as an 8P8C (commonly referred to as an RJ45 connector), an IEEE-1394 connection (commonly referred to as FireWire, DV, or i.Link), or the like.

In some embodiments, the antenna 28 allows for wireless communication with the network 29. The antenna 28 may allow connection to the network 29 via cellular communications network or a wireless communications network such as Wi-Fi in a home.

The communications port 26 and the antenna 28 allow data to be communicated from the system 10 to the network 29 or a home computing system, for instance, for analysis and/or review.

The network 29 may be almost any type of network and may interface with the system 10 in a variety of ways. For example, in some embodiments, the network 29 may interface by optical and/or electronic interfaces, and/or may use a plurality of network topographies and/or protocols including, but not limited to, Ethernet, TCP/IP, circuit switched path, combinations thereof, and/or the like. For example, in some embodiments, the network 29 may be a version of an Internet network (e.g., exist in a TCP/IP-based network). Additionally, the network 29 may use a variety of network protocols to permit bi-directional interface and/or communication of data and/or information between the system 10 and a storage server 31, for instance. It is conceivable that in the near future, embodiments of the present disclosure may use more advanced networking technologies.

In some embodiments, the storage server 31 may be provided operably connected to the network 29. In one embodiment of the system 10, data, including video and/or sound, may be uploaded to the storage server 31 via the network 29. In one embodiment, the data may be uploaded substantially in real time as the videos and/or sound is captured. In another embodiment, the data may be stored in the memory 16 and uploaded when the system is connected to the network 29 via the communications port 26. In another embodiment, the data may be cached in the memory 16 and uploaded as a connection to the network 29 as becomes available.

The storage server 31 may be a network-based or cloud-based server provided with a user interface delivered through one or a series of web pages that allows an end user to access videos and/or sound that have been uploaded and stored on the storage server 31. It should be noted that the user interface of the system 10 may be another type of interface including, but not limited to, a Windows-based application, a mobile device based application, a mobile web interface, and/or the like. Moreover, it is contemplated that end users may share the images stored in association with the storage server via a social media community that provides the ability for users to view images and resulting analyses. The community may further provide the ability to comment on images, compare images, comment on analyses and compare analyses. The community may further include announcements regarding events and other things that may be of interest to people that golf.

As used herein, the terms "network-based," "cloud-based," and any variations thereof, are intended to include the provision of configurable computational resources on demand via interfacing with a computer and/or computer network, with software and/or data at least partially located on a computer and/or computer network.

In some embodiments, the image processor 14 and the main processor 20 may work together or independently to execute the software 27 stored on the memory 16. Exemplary embodiments of the image processor 14 and the main processor 20 may include, but are not limited to, a digital signal processor (DSP), a central processing unit (CPU), a field programmable gate array (FPGA), a microprocessor, a multi-core processor, combinations, thereof, and/or the like, for example.

The system 10 may be provided with logic embodied in the form of software 27 stored in the memory 16 that may be executed on the image processor 14 and/or the main processor 20. The software 27, when executed by the image processor 14 and/or the main processor 20, may cause the system 10 to capture a golf swing and/or the flight of a golf ball as a series of images using the camera 22 and sound using the microphone 24 and analyze the captured golf swing and/or resulting golf ball flight using the main processor 20.

The software 27 when executed by the image processor 14 and/or the main processor 20, may cause the system 10 to recognize when a golfer approaches a ball to swing and cause the system to save captured images. For instance, in one embodiment, the software 27 may be programmed to analyze images captured by the camera 22 and temporarily cached in the memory 16 to determine when a golfer approaches the ball. When the software 27 determines that the golfer has approached the golf ball to swing, the software 27 may be programmed to cause the processor 20 to begin permanently saving images captured by the camera 22 in the memory 16. The software 27 may be programmed to permanently save captured images from the golfer's backswing as well as the full flight of the ball. Based on the captured images, the software 27 may be programmed to cause the main processor 20 to analyze the golfer's swing and/or golf ball flight path.

To determine when the golfer steps in front of the camera, the software 27 may include an artificial intelligence algorithm programmed to separate blobs from the background and know when a swing takes place based on shapes. The artificial intelligence algorithm may be further programmed to anticipate the trajectory of the ball based on swing characteristics to assist the system 10 in tracking and recording the entire flight of the ball.

In one embodiment of the system 10, the cache of batteries 32 may consist of rechargeable cells such as 18650 lithium-ion cells operably connected to a charging circuit 33 (shown in FIG. 3). The charging circuit 33 may be configured to recharge the cache of batteries 32 to enable long-term use of the system 10 on the golf course, for instance, where a power source is not readily available. In addition to providing power, the cache of batteries 32 is positioned in the bottom housing 42 such that the cache of batteries 32 provides weight/mass to stabilize the system 10 when placed on the ground or other surface. As shown in FIG. 1, in a preferred approach, the charging circuit 33 may be inductively coupled to a charging base 35, which provides power to the charging circuit 33 such that the charging circuit can recharge the rechargeable cells. In another approach, the charging circuit 33 may receive electric power via a wired connection, such as communications port 26 or proprietary port 34 (both shown in FIG. 4).

The two component housing 30 is provided with a top housing 40 and a bottom housing 42. The top housing 40 connected to the bottom housing 42 such that the top housing 40 can rotate at least 180, 270, and/or even 360 degrees about a central axis of the bottom housing 42 and tilt as much as 25, 45, 90 and/or even 150 degrees from the central axis of the bottom housing 42.

In the embodiment illustrated in FIGS. 1-3, the bottom housing 42 is provided with a ball 50 and the top housing 40 is provided with a socket 52, the ball 50 connectable to the socket 52 to form a ball and socket joint. The two housings will be attached via the ball and socket joint with suitable tension such that the top and bottom housing will be capable of tilting and rotating relative to one another. In other embodiments, the two component housing 30 may further be provided with a collar threadably connected to the top housing 40 such that the top housing 40 may be moved to a desired angle relative to the bottom housing 42 and tightening the collar locks the top housing 40 at the desired angle. Loosening the collar allows the top housing 40 to be repositioned relative to the bottom housing 42 and locked in place by tightening the collar. It should be noted that the embodiment shown is for illustration purposes only and that any joint that allows the relative movement between the top housing 40 and the bottom housing 42 described herein may be used.

The top housing 40 is provided with a conical portion 70 and the bottom housing 42 is provided with a conical portion 72. The ball 50 forms a vertex of conical portion 72 and is connected to the socket 52 which forms a vertex of conical portion 72 of the top housing 40 such that the two component housing 30 forms an hourglass shape. From any angle, the hourglass shape presents the same wind load making the two component housing 30 more stable when placed, for instance, on a tee box or fairway.

In the illustrated embodiment, the top housing 40 is provided with a cap portion 74 that is attachable to the conical portion 70. The cap portion 74 may be configured to house the camera 22, the microphone 24, and the speaker 25.

In the illustrated embodiment, the bottom housing 42 is provided with a base portion 76 that is attachable to the conical portion 72. The base portion 76 may be configured to accept the cache of batteries 32 and the microprocessor 12.

Figure 4:
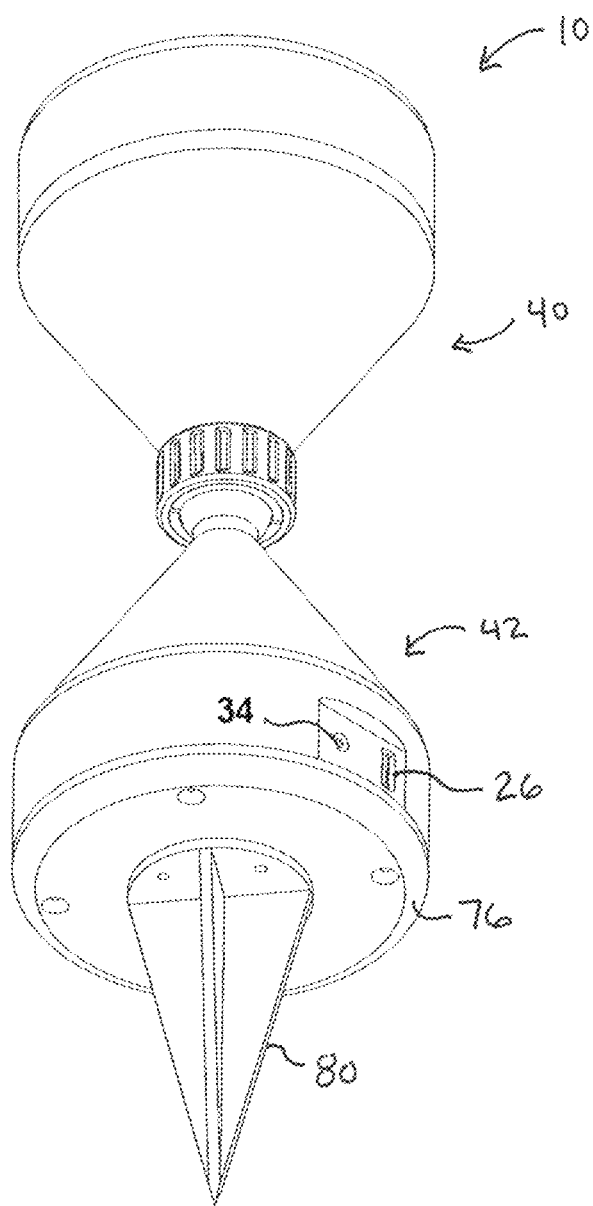
FIG. 4 is a rear perspective view of a system for analyzing a golf swing and/or golf ball flight path constructed in accordance with one embodiment of the present disclosure.

As illustrated in FIG. 4, the system 10 may further be provided with a spike 80 that is preferably removably attached to the base portion 76 of the bottom housing 42 using a component that allows the user to attach and remove the spike as needed on the course, such mechanism that allows the spike to slide and click into place. When connected, the spike 80 may be driven into the ground to further stabilize the two component housing 30.

In another embodiment of the two component housing 30, an additional weight (not shown) may be removably attached to (or enclosed within) the bottom housing 42 to further stabilize the two component housing 30.

From the above description, it is clear that the inventive concept(s) disclosed herein are well adapted to carry out the objects and to attain the advantages mentioned herein, as well as those inherent in the inventive concept(s) disclosed herein. While the embodiments of the inventive concept(s) disclosed herein have been described for purposes of this disclosure, it will be understood that numerous changes may be made and readily suggested to those skilled in the art which are accomplished within the scope and spirit of the inventive concept(s) disclosed herein.

What is claimed is:

1. An apparatus comprising:
an image processor;
memory;
a communications circuit;
a main processor operably connected to the image processor, the memory, and the communications circuit;
a cache of batteries for providing power to the image processor, the memory, the communications circuit, and the main processor;
a camera lens; and
a two component housing comprising a bottom housing component and a top housing component, the bottom housing component sized to receive and encapsulate at least the cache of batteries there within, and the top housing component supporting the camera lens, said top housing component being operably attached to the bottom housing component such that the top housing component can rotate about a central axis of the bottom housing component and tilt from the central axis.

2. The apparatus of claim 1 wherein the communications circuit transmits and receives data in accord with one or more communications protocols selected from the group comprising 4G, 5G, Bluetooth, FTP, HTTP, HTTPS, MMS, PPP, SMTP, SMS, SSL, TLS, TCP/IP, Wi-Fi, and Wi-Max.

3. The apparatus of claim 2 further comprising a communications port operably connected to the communications circuit such that data can be transmitted and received over a wired connection.

4. The apparatus of claim 3 further comprising an antenna operably connected to the communications circuit such that data can be transmitted and received over a wireless connection.

5. The apparatus of claim 2 further comprising an antenna operably connected to the communications circuit such that data can be transmitted and received over a wireless connection.

6. The apparatus of claim 4 further comprising a microphone operably connected to the main processor.

7. The apparatus of claim 6 further comprising an audio speaker operably connected to the main processor.

8. The apparatus of claim 7 further comprising a spike attached to the bottom housing component.

9. The apparatus of claim 8 further comprising a motor operably connected to the top housing component so as to selectively rotate and maintain the top housing component in a desired position.

10. The apparatus of claim 9 wherein the motor is operably connected to the main processor such that the main processor commands the motor to move the top housing component.

11. The apparatus of claim 10 wherein the cache of batteries is comprised of rechargeable batteries, the apparatus further comprises a charging circuit operably associated with the cache of batteries.

12. A system comprising:
a web storage server;
a first interface to the web storage server that allows end users to access video stored on the web storage server;
a second interface to the web storage server;
one or more apparatuses each being capable of operably connecting via the second interface to upload video, each of the apparatuses comprising:
an image processor;
memory;
a communications circuit for connecting to the second interface;
a main processor operably connected to the image processor, the memory, and the communications circuit;
a cache of batteries for providing power to the image processor, the memory, the communications circuit, and the main processor;
a camera lens; and
a two component housing comprising a bottom housing component and a top housing component, the bottom housing component sized to receive and encapsulate at least the cache of batteries there within, and the top housing component supporting the camera lens, said top housing component being operably attached to the bottom housing component such that the top housing component can rotate about a central axis of the bottom housing component and tilt from the central axis.

* * * * *